United States Patent
Cravo et al.

(10) Patent No.: US 9,035,048 B2
(45) Date of Patent: May 19, 2015

(54) TETRAHYDROTRIAZINE COMPOUNDS FOR TREATING DISEASES ASSOCIATED WITH AMPK ACTIVITY

(75) Inventors: Daniel Cravo, Montesson (FR); Sophie Hallakou-Bozec, Montrouge (FR); Didier Mesangeau, Combs la Ville (FR); Samer Elbawab, Bures sur Yvette (FR)

(73) Assignee: POXEL, Lyons (FR)

( * ) Notice: Subject to any disclaimer, the term of this patent is extended or adjusted under 35 U.S.C. 154(b) by 339 days.

(21) Appl. No.: 12/998,848

(22) PCT Filed: Dec. 11, 2009

(86) PCT No.: PCT/EP2009/066999
§ 371 (c)(1),
(2), (4) Date: Jun. 8, 2011

(87) PCT Pub. No.: WO2010/066901
PCT Pub. Date: Jun. 17, 2010

(65) Prior Publication Data
US 2011/0236317 A1 Sep. 29, 2011

(30) Foreign Application Priority Data
Dec. 12, 2008 (EP) ..................... 08021618

(51) Int. Cl.
*C07D 251/10* (2006.01)
*A61K 31/53* (2006.01)
*A61P 35/00* (2006.01)

(52) U.S. Cl.
CPC ............. *C07D 251/10* (2013.01); *A61K 31/53* (2013.01)

(58) Field of Classification Search
CPC .................................................. A61K 31/53
USPC .............. 544/204, 206, 208, 209; 514/245
See application file for complete search history.

(56) References Cited

U.S. PATENT DOCUMENTS 7,034,021 B2 * 4/2006 Moinet et al. ............... 514/245
2003/0109530 A1 6/2003 Moinet

FOREIGN PATENT DOCUMENTS

DE 601 21 294 8/2007
WO WO 2007/079916 7/2007
WO WO 2007/079917 7/2007

OTHER PUBLICATIONS

Tulipano et al. Endocrine (2012) 42: 292-298.*
Hardie et al., Chemistry and Biology 19, 1222-1236, 2012.*
Giordanetto et al. Expert Opin. Ther. Patents (2012) 22(12): 1467-1477.*
Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Rattan et al. J. Biol. Chem. 2005, 280:39582-39593.*
International Search Report for PCT/EP2009/066999, mailed Jun. 14, 2010.
Kuhajda, "AMP-activated protein kinase and human cancer: cancer metabolism revisited", International Journal of Obesity (2008) 32, 536-541.
Sag et al, "Adenosine 5'-Monophosphate-Activated Protein Kinase Promotes Macrophage Polarization to an Anti-Inflammatory Functional Phenotype", J Immunol 2008; 181:8633-8641.
Zadra et al, "A novel direct activator of AMPK inhibits prostate cancer growth by blocking lipogenesis", EMBO Molecular Medicine, 2014, vol. 6, No. 4, pp. 519-538.

* cited by examiner

*Primary Examiner* — Venkataraman Balasubramanian
(74) *Attorney, Agent, or Firm* — Nixon & Vanderhye P.C.

(57) ABSTRACT

The invention relates to compounds of formula (I) wherein the radicals $R^1$ to $R^6$ have the meaning according to claim 1, and/or physiologically acceptable salts thereof, for the prophylactic or therapeutic treatment and/or monitoring of physiological and/or pathological conditions that are associated with the activity of AMP-activated protein kinase (AMPK). Another object of the invention concerns the use of said compounds for enhancing glucose homeostasis, improving podocytopathy and/or decreasing the production of reactive oxygen species (ROS). The invention also relates to a method for in-vitro diagnosing diabetic nephropathy and a method for screening compounds that reduce podocytopathy, in each case by applying synaptopodin as biomarker.

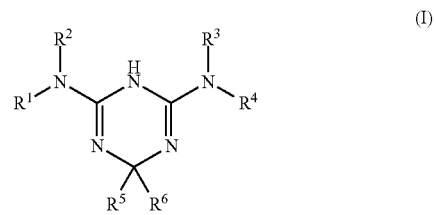

4 Claims, 2 Drawing Sheets

TETRAHYDROTRIAZINE COMPOUNDS FOR TREATING DISEASES ASSOCIATED WITH AMPK ACTIVITY

This application is the U.S. national phase of International Application No. PCT/EP2009/066999, filed 11 Dec. 2009, which designated the U.S., and claims priority to EP Application No. 08021618.7, filed 12 Dec. 2008, the entire contents of which is hereby incorporated by reference.

The invention relates to compounds of formula (I)

wherein the radicals $R^1$ to $R^6$ have the meaning described below, and/or physiologically acceptable salts thereof, for the prophylactic or therapeutic treatment and/or monitoring of physiological and/or pathological conditions that are associated with the activity of AMP-activated protein kinase (AMPK). Another object of the invention concerns the use of said compounds for enhancing glucose homeostasis, improving podocytopathy and/or decreasing the production of reactive oxygen species (ROS). The invention also relates to a method for in-vitro diagnosing diabetic nephropathy and a method for screening compounds that reduce podocytopathy, in each case by applying synaptopodin as biomarker.

AMPK is well established as a sensor and regulator of cellular energy homeostasis (Hardie & Hawley, Bioassays 23, 1112 (2001); Kemp et al., Biochem. Soc. Transactions 31, 162 (2003)). Allosteric activation of this kinase due to rising AMP levels occurs in states of cellular energy depletion. The resulting serine/threonine phosphorylation of target enzymes leads to an adaptation of cellular metabolism to low energy state. The net effect of AMPK activation induced changes is inhibition of ATP consuming processes and activation of ATP generating pathways, and therefore regeneration of ATP stores. Examples of AMPK substrates include acetyl-CoA carboxylase (ACC) and HMG-CoA reductase (Carling et al., FEBS letters 223, 217 (1987)). Phosphorylation and therefore inhibition of ACC leads to a decrease in fatty acid synthesis (ATP-consuming) and at the same time to an increase in fatty acid oxidation (ATP-generating). Phosphorylation and resulting inhibition of HMG-CoA reductase leads to a decrease in cholesterol synthesis. Other substrates of AMPK include hormone sensitive lipase (Garton et al., Eur. J. Biochem. 179, 249 (1989)), glycerol-3-phosphate acyl transferase (Muoio et al., Biochem. J. 338, 783 (1999)) and malonyl-CoA decarboxylase (Sarah et al., JBC 275, 24279 (2000)).

AMPK is also implicated in the regulation of liver metabolism. Elevated glucose production by the liver is a major cause of fasting hyperglycemia in type II diabetes (T2D) (Saltie) et al., Cell 10, 517 (2001)). Gluconeogenesis in the liver is regulated by multiple enzymes such as phosphoenolpyruvate carboxykinase (PEPCK) and glucose-6-phosphatase (G6Pase). Activation of AMPK suppresses the transcription of theses genes in hepatoma cells (Lochhead et al., Diabetes 49, 896 (2000)).

AMPK activation also down-regulates gluconeogenesis acting on some other genes expression. These effects may be due to its ability to down-regulate key transcription factors, such as SREBP-1c (Zhou et al., J. Clin. Invest. 108, 1167 (2001)) and ChREBP (Kawaguchi et al., JBC 277, 3829 (2002); Leclerc et al., Diabetes 50, 1515 (2001)), or by direct phosphorylation of transcriptional co-activators, such as p300 (Yang et al., JBC. 276, 38341(2001)) and TORC2.

AMPK is considered as an attractive candidate for contraction-induced skeletal muscle glucose uptake because it is activated in parallel with elevation in AMP and a reduction in creatine phosphate energy stores (Hutber et al., Am. J. Physiol. Endocrinol. Metab. 272, E262 (1997)). Furthermore, AICAR-induced activation of AMPK increases glucose uptake (Merrill et al., Am. J. Physiol. Endocrinol. Metab. 273, E1107 (1997)) concomitantly with glucose transporter 4 (GLUT4) fusion with plasma membrane (Kurth-Kraczek, Diabetes 48, 1667 (1999)). Over expression of a kinase dead subunit in skeletal muscle abolishes 5-aminoimidazole-4-caboxamide-1beta-riboside (AICAR), but partially impairs contraction-stimulated glucose uptake (Mu et al., Mol. Cell. 7, 1085 (2001)). These findings suggest that additional pathways mediate contraction induced glucose uptake whereas it is apparent that AMPK mediates the effects of AICAR on glucose uptake.

Despite extensive study on upstream stimuli that activate AMPK, investigation on the downstream substrate(s) of AMPK-mediated glucose uptake is lacking. More recent reports revealed that Akt substrate of 160 kDa (AS160) is an important substrate downstream of Akt that is involved in insulin-stimulated glucose uptake. In addition to insulin, contraction and activation of AMPK by AICAR is associated with increased phosphorylation of AS160 in rodent skeletal muscle. Phosphorylation of AS160 is impaired or abolished in skeletal muscle from AMPK a2 knockout, g3 knockout, and a2-kinase dead mice in response to AICAR treatment (Treeback et al., Diabetes 55, 2051 (2006)). This corroborates findings of impaired AICAR-stimulated glucose uptake in skeletal muscle of these mice (Jorgensen et al., JBC 279, 1070 (2004)). Therefore, AS160 appeared to be a downstream target of AMPK in mediating glucose uptake in skeletal muscle.

Taken together all these metabolic effects provide evidence that AMPK suppresses liver gluconeogenesis and lipid production, while decreasing hepatic lipid deposition via increased lipid oxidation, thus improving the glucose and lipid profile in T2D.

More recently an involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle (Minokoshi et al., Nature 415, 339 (2002)). Adiponectin another adipocyte derived hormone leading to improved carbohydrate and lipid metabolism, has been demonstrated to stimulated AMPK liver and skeletal muscle (Yamanauchi et al., Nature Medicine 8, 1288 (2002); Tomas et al., PNAS 99, 16309 (2002)). The activation of AMPK in these circumstances seems to be independent of increasing cellular AMP levels but rather due to phosphorylation by one or more yet to be identified upstream kinases.

Based on the knowledge of the above-mentioned consequences of AMPK activation, profound beneficial effects would be expected from in-vivo activation of AMPK. In liver, decreased expression of gluconeogenic enzymes would reduce hepatic glucose output and improve overall glucose homeostasis, and both direct inhibition and/or reduced expression of key enzymes in lipid metabolism would increase glucose uptake and fatty acid oxidation with resulting improvement of glucose homeostasis and, due to a reduction in intra-myocyte triglyceride accumulation, improved insulin action. Finally, the increase in energy expenditure should lead to a decrease in body weight. The combination of these effects in the metabolic syndrome would be expected to significantly reduce the risk for acquiring cardiovascular diseases.

Several studies in rodents support this hypothesis (Bergeron et al., Diabetes 50, 1076 (2001); Song et al., Diabetologia 45, 56 (2002); Halseth et al., Biochem. and Biophys. Res. Comm. 294, 798 (2002); Buhl et al., Diabetes 51, 2199 (2002)). Until recently most in-vivo studies have relied on the AMPK activator AICAR, a cell permeable precursor of ZMP. ZMP acts as an intracellular AMP mimic and, when accumulated to high enough levels, is able to stimulate AMPK activity (Corton et al., Eur. J. Biochem. 229, 558 (1995)). However, ZMP also acts as an AMP mimic in the regulation of other enzymes, and therefore not a specific AMPK activator (Musi & Goodyear, Curr Drug Targets Immune Endocr Metabol Disord 2, 119 (2002)). Several in-vivo studies have demonstrated beneficial effects of both acute and chronic AICAR administration in rodent models of obesity and T2D (Bergeron et al., Diabetes 50, 1076 (2001); Song et al., Diabetologia 45, 56 (2002); Halseth et al., Biochem. Biophys. Res. Comm. 294, 798 (2002); Buhl et al., Diabetes 51, 2199 (2002)). For example, 7 week AICAR administration in the obese Zucker (fa/fa) rat leads to a reduction in plasma triglycerides and free fatty acids, an increase in HDL cholesterol, and a normalization of glucose metabolism as assessed by an oral glucose tolerance test (Minokoshi et al., Nature 415, 339 (2002)). In both ob/ob and db/db mice, 8 day AICAR administration reduces blood glucose by 35% (Halseth et al., Biochem. Biophys. Res. Comm. 294, 798 (2002)). In addition to AICAR, it was found that the diabetes drug metformin can activate AMPK in-vivo at high concentrations (Zhou et al., J. Clin. Invest. 108, 1167 (2001); Musi et al., Diabetes 51, 2074 (2002)), although it has to be determined to what extent its anti-diabetic action relies on this activation. As with leptin and adiponectin, the stimulatory effect of metformin is indirect via activation of an upstream kinase (Zhou et al., J. Clin. Invest. 108, 1167 (2001)).

More recently, a small molecule AMPK activator have been described. This direct AMPK activator, named A-769662, a member of the thienopyridone family in-vivo induces a decrease in plasma glucose and triglycerides (Cool et al., Cell Metab. 3, 403 (2006)).

In addition to pharmacologic intervention, several transgenic mouse models have been developed in the last years, and initial results are becoming available. Expression of dominant negative AMPK in skeletal muscle of transgenic mice has demonstrated the AICAR effect on stimulation of glucose transport is dependant of AMPK activation (Mu et al., Molecular Cell 7, 1085 (2001)), and therefore likely not caused by non-specific ZMP effects. Similar studies in other tissues will help to further define the consequences of AMPK activation. It is expected that pharmacologic activation of AMPK will have benefits in the metabolic syndrome with improved glucose and lipid metabolism and a reduction in body weight. To qualify a patient as having metabolic syndrome, three out of the five following criteria must be met: elevated blood pressure above 130/85 mm Hg, fasting blood glucose above 110 mg/dl, abdominal obesity above 40" (men) or 35" (women) waist circumference, and blood lipid changes as defined by increase in triglycerides above 150 mg/dl or decrease of HDL cholesterol below 40 mg/dl (men) or 50 mg/dl (women). Therefore, the combined effects that may be achieved through activation of AMPK in a patient who qualifies as having metabolic syndrome would raise the interest of this target.

Stimulation of AMPK has been shown to stimulate expression of the uncoupling protein 3 (UCP3) skeletal muscle (Zhou et al., Am. J. Physiol. Endocrinol. Metab. 279, E622 (2000)) and might therefore be a way to prevent damage from reactive oxygen species. Endothelial NO synthase (eNOS) has been shown to be activated through AMPK mediated phosphorylation (Chen et al., FEBS Letters 443, 285 (1999)), therefore AMPK activation can be used to improve local circulatory systems.

AMPK has a role in regulating the mTOR pathway. Mammalian target of rapamycin (mTOR) is a serine/threonine kinase and a key regulator of protein synthesis. To inhibit cell growth and protect cells from apoptosis induced by glucose starvation, AMPK phosphorylates TSC2 at Thr-1227 and Ser-1345 increasing the activity of the TSC1 and TSC-2 complex to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signaling pathway. Treatment of various cancer cell lines by AICAR attenuated the cell proliferation both in-vitro and in-vivo studies (Rattan et al., JBC 280, 39582 (2005)). Reports link the treatment of metformin with a lower risk of cancer in diabetic patients (Evans et al., BMJ 330, 1304 (2005)). The activation of AMPK by AICAR has been shown to reduce expression of the lipogenic enzymes FAS and ACC, resulting in suppression of proliferation in prostate cancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

It has been described that AICAR as an AMPK activator exerts anti-inflammatory diseases. It has been observed that AICAR attenuates the production of pro-inflammatory cytokines and mediators (Gin et al., J. Neuroscience 24, 479 (2004)). AICAR in rat model and in-vitro attenuates EAE progression by limiting infiltration of leucocytes across blood brain barrier (BBB) (Nath et al., J. Immunology 175, 566 (2005); Prasad et al., J. Neurosci Res. 84, 614 (2006)), and it has been suggested recently that AMPK activating agents act as anti-inflammatory agents and can hold a therapeutic potential in Krabbe disease/twitcher disease (an inherited neurological disorder) (Gin et al., J. Neurochem. 105, 1820 (2008)).

It has also taught in the prior art that AMPK activation induced AMPK activators can prevent renal hypertrophy as seen in early stages of insulin deficient diabetes in association with increased AMPK phosphorylation in the renal cortex. The mechanism of action might be induced by negative control of AMPK on mTOR (Lee et al., Am J Renal Physiol 292, F617 (2007)) and decreased renal hypertrophy by reduction of protein synthesis.

Therefore, the technical problem forming the basis of the present invention is to provide compounds allowing an effective application in the prevention or therapy of diseases that are associated with AMPK activity, especially such compounds that improve the therapeutic efficacy and minimize adverse effects.

The present invention solves this problem by providing compounds of formula (I):

in which
R¹, R² each, independently of one another, denote H or A,
R³, R⁴ each, independently of one another, denote H, A, alkenyl having 2-6 C atoms, alkynyl having 2-6 C atoms, Ar or Het,
R⁵ and R⁶ together also denote alkylene having 2, 3, 4 or 5 C atoms,
R⁵, R⁶ each, independently of one another, denote H, A, $(CH_2)_nAr$, $(CH_2)_mOAr$, $(CH_2)_mOA$ or $(CH_2)_mOH$,
R⁵ and R⁶ together also denote alkylene having 2, 3, 4 or 5 C atoms, in which one $CH_2$ group may be replaced by O, NH or NA and/or in which 1H atom may be replaced by OH,
Ar denotes phenyl, naphthyl or biphenyl, each of which is unsubstituted or mono-, di- or trisubstituted by Hal, A, OA, OH, COOH, COOA, CN, $NH_2$, NHA, $NA_2$, $SO_2A$ and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, OH, OA, $NH_2$, $(CH_2)_nAr$, NHA, $NA_2$, COOH, COOA and/or =O (carbonyl oxygen),
A denotes unbranched or branched alkyl having 1-10 C atoms, in which 1-7 H atoms may be replaced by F, or cyclic alkyl having 3-7 C atoms,
Hal denotes F, Cl, Br or I,
m denotes 1, 2, 3, 4, 5 or 6, and
n denotes 0, 1 or 2,
and/or physiologically acceptable salts thereof for the prophylactic or therapeutic treatment and/or monitoring of diseases that are caused, mediated and/or propagated by the activity of AMP-activated protein kinase.

It has been surprisingly demonstrated by the inventors that the tetrahydrotriazine compounds of formula (I) and derivatives thereof can be applied in medicaments in order to tackle medical indications arising from AMPK activity, especially a lack in said activity, such as renal hypertrophy and diabetic nephropathy, and diseases being linked therewith. Before filing this application, it has only been known that compounds of formula (I) can be prepared by processes according to WO 2001/55122. The compounds might be useful in the treatment of diseases associated with the IR syndrome. Representatives are currently under clinical evaluation. But now, said tetrahydrotriazine compounds underlying the invention have been found to improve the overall glucose homeostasis. The present invention reveals a strong AMPK activation while the glomerular content of synaptopodin is restored and the ROS production is decreased. These phenomena are stimulated by the impact of the compounds of formula (I), which forms the basis of the inventive remedy for such specified clinical pictures as renal hypertrophy and diabetic nephropathy.

The compounds of the invention exhibit very valuable pharmacological properties along with good tolerability. In comparison with a standard therapy, mainly involving ACE inhibitor drugs, whose goal of treatment is to slow the progression of kidney damage and control related complications, the tetrahydrotriazine compounds face the basic cause of AMPK-mediated diseases. Consequently, the aforementioned compounds represent a novel medicament that is well suited for the prophylaxis, treatment and/or monitoring of AMPK-mediated diseases. More particular, the inventive compounds give a potent drug against renal hypertrophy and diabetic nephropathy for a broad range of patients.

Said biological activities of the compounds of the invention may be determined by techniques known to the skilled artisan. Suitable experimental animals are, for example, mice, rats, guinea-pigs, dogs, cats, apes or pigs. For example, the gold standard for the in-vivo assessment of IR is the euglycemic-hyperinsulinemic glucose clamp. Other tools are the homeostasis model assessment of insulin resistance (HOMA-IR) test or the frequently sampled oral glucose tolerance test (OGTT). Techniques that are suitable to determine changes in insulin sensitivity have to be sensitive, reproducible, operationally simple and relatively high-throughput.

In the meaning of the present invention, the compounds of formula (I) are defined to include pharmaceutically usable derivatives comprising solvates, prodrugs, tautomers, enantiomers, racemates and stereoisomers thereof, including mixtures thereof in all ratios. Preference is given to solvates and/or physiologically acceptable salts, more preferably physiologically acceptable salts, most preferably physiologically acceptable acid-addition salts.

The term "solvates" of the tetrahydrotriazine derivatives is taken to mean adductions of inert solvent molecules onto the compounds, which are formed owing to their mutual attractive force. Solvates are, for example, mono- or dihydrates or alkoxides.

The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61 (1995). The compounds of the invention can be obtained by liberating it from their functional derivatives by solvolysis, in particular hydrolysis, or by hydrogenolysis. It is likewise possible for the compounds of the invention to be in the form of any desired prodrugs, such as esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth et al., The Practice of Medicinal Chemistry 31, 671, Academic Press (1985); Bundgaard, Design of Prodrugs, Elsevier (1985); Bundgaard, A Textbook of Drug Design and Development 5, 131, Harwood Academic Publishers (1991)). It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers.

Formula (I) also encompasses the optically active forms (stereoisomers), such as the enantiomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. For example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds. The pharmaceutical composition may also comprise mixtures of the compound and at least a single derivative, or mixtures of derivatives, respectively, which may comprise solvates and/or salts, for instance.

The nomenclature as used herein for defining compounds, especially the compounds according to the invention, is in general based on the rules of the IUPAC-organization for chemical compounds and especially organic compounds. The terms indicated for explanation of the above compounds of the invention always, unless expressly indicated otherwise in the description or in the claims, have the following meanings:

Above and below, the radicals $R^1$, $R^2$, $R^3$, $R^4$, $R^5$, $R^6$ have the meanings indicated for the formula (I), unless expressly indicated otherwise.

A denotes unbranched (linear) or branched alkyl having 1-10 C atoms, in which 1-7H atoms may be replaced by F, or cyclic alkyl having 3-7 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl. Furthermore, A preferably denotes alkyl having 1, 2, 3, 4, 5 or 6 C atoms, more preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Very particularly preferably, A denotes methyl.

Cyclic alkyl (cycloalkyl) preferably denotes cyclopropyl, cyclobutyl, cyclopentyl, cyclohexyl or cycloheptyl.

Alkenyl has 2, 3, 4, 5 or 6 C atoms and preferably denotes vinyl or propenyl.

Alkynyl has 2, 3, 4, 5 or 6 C atoms and preferably denotes CECH or CEC-CH₃.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonyl)phenyl, o-, m- or p-cyanophenyl, o-, m- or p-carboxyphenyl, o-, m- or p-methoxycarbonylphenyl, o-, m- or p-acetylphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-amino-4-chloro-, 2-amino-3-chloro-, 2-amino-4-chloro-, 2-amino-5-chloro- or 2-amino-6-chlorophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-fluoro-4-methoxyphenyl, 3-amino-6-methylphenyl or 2,5-dimethyl-4-chlorophenyl. Ar particularly preferably denotes phenyl, hydroxyphenyl or methoxyphenyl.

Irrespective of further substitutions, Het denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2, 4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4 or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated. Irrespective of further substitutions, Het can thus, for example, also denote 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3, 4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2- oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindolyl, 2-oxo-1,3-dihydroindolyl or 2-oxo-2,3-dihydrobenzimidazolyl.

Het preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl or benzo-2,1,3-thiadiazolyl, each of which is unsubstituted or mono-, di- or trisubstituted by A, CODA, Hal and/or =O (carbonyl oxygen).

$R^1$ and $R^2$ preferably denote A. $R^3$ and $R^4$ preferably denote H. $R^5$ preferably denotes H. $R^6$ preferably denotes A. More preferably, R' and $R^2$ denote methyl, $R^3$ and $R^4$ denote H, $R^5$ denotes H, and $R^6$ denotes methyl.

In a most preferably embodiment of the present invention, the compound comprises 5,6-dihydro-4-dimethylamino-2-imino-6-methyl-1,3,5-triazine and/or the hydrochloride salt thereof. This compound is a tautomer of the compound synthesized in example 1 (4-amino-3,6-dihydro-2-dimethylamino-6-methyl-1,3,5-triazine hydrochloride). In a highly preferred embodiment of the present invention, the compound comprises the enantiomer (+) 5,6-dihydro-4-dimethylamino-2-imino-6-methyl-1,3,5-triazine and/or the hydrochloride salt thereof.

The triazine derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

According to EP 1 250 328 B1, whose disclosure is incorporated in its entirety by reference herein, the compounds of formula (I) can be prepared by reacting a compound of formula (II)

II in which
$R^1$, $R^2$, $R^3$, $R^4$ have the meanings indicated above,
with a compound of the formula (III), (IV) or (V)

(III)

(IV)

(V)

in which
$R^5$, $R^6$ have the meanings indicated above, and
R7 is a methyl or ethyl group,
wherein the reaction is performed in a polar solvent (e.g. ethanol or dimethylformamide) and in the presence of an organic (e.g. camphorsulfonic acid) or inorganic acid (e.g. hydrochloric acid).

It is preferred, however, that the compounds of the formula (I) are prepared by a process, which comprises the reaction of a compound of the formula (II)

II in which
$R^1$, $R^2$, $R^3$, $R^4$ have the meanings indicated above,
with a compound of the formula (VI)

III in which
$R^5$, $R^6$ have the meanings indicated above.

Surprisingly, investigations in the course of the synthesis of dihydro-1,3,5-triazinamine derivatives showed that the compounds of formula (I) can be obtained in at least comparable or higher yield compared to the prior art. Crucial advantages that may be mentioned here are a considerably shorter reaction time and fewer waste products. This consequently also means considerably lower energy consumption. One molecule of water is liberated in the process according to the invention per molecule of compound of the formula (I) formed. In the prior-art process, two molecules of alcohol are liberated per molecule of compound of the formula (I) formed.

Metformin as preferred starting material has the structure:

The compounds having the general formula (II) are biguanides, the synthesis of which is mastered by the average person skilled in the art. Some publications in which the synthesis of such compounds is described are cited by way of example (FR 1 537 604; FR 2 132 396; Slotta & Tschesche, Ber. 62b, 1398 (1929); Shapiro et al., J. Org. Chem. 81, 3725, 3728, 4636 (1959)).

The reaction of the compounds of the formulae (II) and (VI) preferably proceeds in a suitable polar solvent, e.g. alcohols, such as methanol, ethanol, isopropanol, n-propanol, n-butanol, isobutanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); esters, such as ethyl acetate, or mixtures of the said solvents. Particular preference is given to isobutanol, furthermore ethanol and isopropanol.

Depending on the conditions used, the reaction time is between a few minutes and 14 days, particularly preferably between 3 and 12 hours. The reaction temperature is between about 50° C. and 150° C., normally between 90° C. and 120° C.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods.

The reaction is preferably carried out in the presence of an organic or inorganic acid. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Also suitable and preferred in the meaning of the present invention are acidic cationic ion exchanger resins, such as the commercially available Dowex® or Amberlyst® resins. More preference is given to p-toluenesulfonic acid, furthermore hydrochloric acid, methanesulfonic acid, sulfuric acid or camphorsulfonic acid, or acidic cationic ion exchanger resins, for example Dowex® 50, Amberlyst® 15 or Dowex® DR-2030. Most preferably, the reaction is carried out in the presence of p-toluenesulfonic acid or an acidic cationic ion exchanger resin.

A base of the formula (I) can also be converted into the associated acid-addition salt using an acid, for example by reaction of equivalent amounts of the base and acid in an inert solvent, such as ethanol, with subsequent evaporation. Particularly suitable acids for this reaction are those which give physiologically acceptable salts. Thus, it is possible to use inorganic acids, for example the aforementioned ones. Salts with physiologically unacceptable acids, for example picrates, can be used for the isolation and/or purification of the compounds of the formula (I).

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

In a very preferred aspect of the present invention, the compound comprises 5,6-dihydro-4-dimethylamino-2-imino-6-methyl-1,3,5-triazine hydrochloride. In another highly preferred embodiment of the present invention, the compound comprises the enantiomeric salt (+) 5,6-dihydro-4-dimethylamino-2-imino-6-methyl-1,3,5-triazine hydrochloride.

As set forth above, the invention relates to a medicament comprising at least one tetrahydrotriazine compound and/or derivatives thereof according to the invention, for the prophylaxis, therapy and/or monitoring of diseases that are caused, mediated and/or propagated by the AMPK activity, and optionally excipients and/or adjuvants. In the meaning of the invention, an "adjuvant" denotes every substance that enables, intensifies or modifies a specific response against the active ingredients of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols. In the meaning of the invention, the term "adjuvant" also includes the expressions "excipient" and "pharmaceutically acceptable vehicle", which denote any solvent, dispersing medium, absorption retardants, etc. that do not cause a side action, for example an allergic reaction, in humans or animals. Consequently, the invention also relates to a pharmaceutical composition comprising as active ingredient an effective amount of at least one compound of formula (I) as defined in the course of the present specification and/or physiologically acceptable salts, thereof together with pharmaceutically tolerable adjuvants, for the prophylactic or therapeutic treatment and/or monitoring of diseases that are caused, mediated and/or propagated by the activity of AMP-activated protein kinase.

The invention additionally relates to a pharmaceutical composition comprising as active ingredient an effective amount of at least one compound of formula (I) and/or physiologically acceptable salts thereof, together with one or more pharmaceutically acceptable adjuvants, for the prophylactic or therapeutic treatment and/or monitoring of diseases that are caused, mediated and/or propagated by the activity of AMP-activated protein kinase.

A "medicament", "pharmaceutical composition" or "pharmaceutical formulation" in the meaning of the invention is any agent in the field of medicine, which comprises one or more tetrahydrotriazine compounds of the invention or preparations thereof and can be used in prophylaxis, therapy, follow-up or aftercare of patients who suffer from diseases, which are associated with AMPK activity, in such a way that a pathogenic modification of their overall condition or of the condition of particular regions of the organism could establish at least temporarily.

Furthermore, the active ingredients may be administered alone or in combination with yet other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. In a preferred embodiment of the present invention, the active ingredient of formula (I) is combined with at least another active ingredient, more preferably an ACE inhibitor, AT1 antagonist, a diuretic, in particular a loop diuretic, HMG-CoA reductase inhibitor and/or salicylate drug, most preferably an ACE inhibitor or AT1 antagonist in combination with a loop diuretic, and/or statin and/or aspirin.

According to another aspect of the invention, the active ingredients are administered either simultaneously or sequentially, preferably in the form of separate pharmaceutical compositions, one comprising the compound of formula (I) in a pharmaceutically acceptable vehicle, the other comprising another compound of formula (I) or another compound of different structural scaffold in a pharmaceutically acceptable vehicle. It shall not be excluded, however, that all active ingredients can be combined in the same pharmaceutical composition and administered, especially if the active ingredients are compounds of formula (I). In the context of the present invention, the terms "pharmaceutical combination" and "combined administration" refers to one or other of these aspects.

In more detail, "combined administration" means, for the purpose of the present invention, fixed and, in particular, free combinations, i.e. either the compound of formula (I) and another active ingredient are present together in one dosage unit, or said compound and said ingredient, which are present in separate dosage units, are administered in direct succession or at a relatively large time interval; a relatively large time interval means a time span up to a maximum of 24 hours. A "dosage unit" means, in particular, a medicinal dosage form in which the release of the active ingredient(s) is achieved with as few problems as possible. This includes, in particular, tablets, coated tablets or pellets, micro-tablets in capsules and solutions with the dosage form advantageously being designed such that the two active-ingredient components are released, or made available effectively for the body, in such a way that an optimal active ingredient profile, and thus action profile, is achieved.

For simultaneous administration as fixed composition, i.e. being a single pharmaceutical formulation with both ingredients, it is prepared, for example, as injection or infusion solution, or lyophilized form thereof, which is filled in ampoules. The fixed composition of the lyophilized form guarantees a simple and secure handling. It is solved in the ampoule by adding an ordinary pharmaceutical injection agent and administered intravenously. The reconstitution solution can be part of the combination package. For use as separate dosage units, these are preferably made available together in one pack and either mixed prior administration or sequentially administered. For example, the two dosage units are packed together in blister packs that are designed with regard to the relative arrangement of the two dosage units with respect to one another, the inscription and/or coloring in a manner known per se so that the times for taking the individual components (dosage regimen) of the two dosage units are evident to a patient. This free combination is of benefit by individually allotting effective amounts of the active ingredients to the patient. Another possibility is the provision of single preparations of said compound and said another active ingredient, i.e. being independent medicaments. The single preparations are converted to contain the required amounts of ingredient for the inventive combination. Corresponding instructions are given at the package insert concerning the combined administration of the respective medicament.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredients with the excipient(s) or adjuvant(s). The pharmaceutical compositions of the invention may be formulated such as to be administered to the patient via a single route (for example by injection) or via different routes (for example orally for the compound of the formula (I) and by injection for another active ingredient).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient(s) to produce a single dosage form varies depending upon the host treated and the particular mode of administration. Suitable excipients include organic or inorganic substances that are suitable for the different routes of administration, such as enteral (e.g. oral), parenteral or topical application, and which do not react with the tetrahydrotriazine compounds of the invention or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions. Thus, for example, in the case of oral administration in the form of a tablet or capsule, the active ingredients can be combined with an oral, non-toxic and pharmaceutically acceptable inert excipient, such as, for example, ethanol, glycerol, water and the like. Powders are prepared by comminuting the compounds of formula (I) to a suitable fine size and mixing it with a pharmaceutical excipient comminuted in a similar manner, such as, for example, an edible carbohydrate, such as, for example, starch or mannitol. A flavor, preservative, dispersant and dye may likewise be present. Capsules are produced by preparing a powder mixture as described above and filling shaped gelatin shells therewith. Glidants and lubricants, e.g. highly disperse silicic acid, talc, magnesium stearate, calcium stearate or polyethylene glycol in solid form, can be added to the powder mixture before the filling operation. A disintegrant or solubiliser, such as agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or betalactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the active ingredients, especially the compounds, comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The active ingredients according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the active ingredients. Syrups can be prepared by dissolving the active ingredients in an aqueous solution with a suitable flavor, while elixirs are prepared using a non-toxic alcoholic vehicle. Suspensions can be formulated by dispersion of the active ingredients, especially the compounds, in a non-toxic vehicle. Solubilisers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can be administered in the form of liposome delivery systems, such as small unilamellar vesicles, large unilamellar vesicles and multilamellar vesicles. Liposomes can be formed from various phospholipids, such as cholesterol, stearylamine or phosphatidylcholines.

The compounds according to the invention can also be fused or complexed with another molecule that promotes the directed transport to the destination, the incorporation and/or distribution within the target cells. The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and cross-linked or amphipathic block copolymers of hydro-gels.

Pharmaceutical formulations adapted for transdermal administration can be administered as independent plasters for extended, close contact with the epidermis of the recipient. Thus, for example, the active ingredients can be delivered from the plaster by iontophoresis, as described in general terms in Pharmaceutical Research 3, 318 (1986).

Pharmaceutical compositions adapted for topical administration can be formulated as ointments, creams, suspensions, lotions, powders, solutions, pastes, gels, sprays, aerosols or oils. For the treatment of the eye or other external tissue, for example mouth and skin, the formulations are preferably applied as topical ointment or cream. In the case of formulation to give an ointment, the active ingredients can be employed either with a paraffinic or a water-miscible cream base. Alternatively, the active ingredients can be formulated to give a cream with an oil-in-water cream base or a water-in-oil base. Pharmaceutical formulations adapted for topical application to the eye include eye drops, in which the active ingredients are dissolved or suspended in a suitable carrier, in particular an aqueous solvent. Pharmaceutical formulations adapted for topical application in the mouth encompass lozenges, pastilles and mouthwashes.

Pharmaceutical formulations adapted for rectal administration can be administered in the form of suppositories or enemas. For the preparation of suppositories, the active principles are mixed in a manner that is known per se with a suitable base constituent, such as polyethylene glycol or semi-synthetic glycerides.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil. Pharmaceutical formulations adapted for administration by inhalation encompass finely particulate dusts or mists, which can be generated by various types of pressurized dispensers with aerosols, nebulisers or insufflators. The compound of formula (I) may be administered by inhalation. For example, aerosols and inhalation methods developed by Inhale Therapeutic Systems, CA, and described in U.S. Pat. No. 5,997,848 make it possible to optimize the absorption and the reproducibility of the dose delivered.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally or as injection solution for parenteral administration, most preferably orally. In particular, the active ingredient is provided in a water-soluble form, such as pharmaceutically acceptable salts, which is meant to include both acid and base addition salts. Furthermore, the active ingredient of the invention and salts thereof may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The respective dose or dosage range for administering the pharmaceutical composition according to the invention is sufficiently high in order to achieve the desired prophylactic or therapeutic effect of reducing symptoms of diseases, which are associated with AMPK activity, as set forth below. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.02 to 1.000 mg, more preferably between 0.5 and 700 mg. It is even most preferred that the unit dose of the compound of formula (I) comprises 1 to 200 mg of said compound.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of AMPK-mediated diseases, particularly renal hypertrophy and/or diabetic nephropathy, is generally in the range from 0.02 to 200 mg/kg of body weight of the recipient (mammal) per day and particularly typically in the range from 12.5 to 150 mg/kg of body weight per day, more preferably from 25 to 100 mg/kg per day, most preferably 40 to 60 mg/kg per day, highly preferably 50 mg/kg per day. Thus, the actual amount per day for an adult mammal weighing 70 kg is usually between 1.4 and 14.000 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions as mentioned in the specification.

Accordingly, the inventive method of treatment can be employed in human and veterinary medicine. According to the invention, the compounds of formula (I) and/or physiologically salts thereof are suited for the prophylactic or therapeutic treatment and/or monitoring of diseases that are associated with AMPK activity. Herein, the compounds can be administered before or following an onset of disease once or several times acting as therapy. The aforementioned medical products of the inventive use are particularly used for the therapeutic treatment. Monitoring is considered as a kind of treatment, wherein the compounds are preferably administered in distinct intervals, e.g. in order to booster the response and eradicate the pathogens and/or symptoms of AMPK-related diseases completely. Either the identical composition or different compositions can be applied. The medicament can also be used to reduce the likelihood of developing a disease or even prevent the initiation of diseases associated with AMPK activity in advance or to treat the arising and continuing symptoms. In the meaning of the invention, prophylactic treatment is advisable if the subject possesses any preconditions for the aforementioned physiological or pathological conditions, such as a familial disposition, a genetic defect, or a previously passed disease.

The diseases as concerned by the application of the compounds of formula (I) are selected from the group of diabetes, pre-diabetes, hyperglycemia, insulin resistance, metabolic syndrome, obesity, renal hypertrophy, renal failure, diabetic nephropathy, neuropathy, diabetic retinopathy, cancer, inflammation, cardiovascular disease and Alzheimer's disease. The tetrahydrotriazine compounds of the invention are also useful for the prophylactic or therapeutic treatment and/or monitoring of physiological and/or pathological conditions of aging. However, in an embodiment of the present invention, the prophylactic or therapeutic treatment and/or monitoring of the following diseases of diabetes, pre-diabetes, hyperglycemia, insulin resistance, obesity, neuropathy, diabetic retinopathy and/or Alzheimer's disease shall be excluded from the matter for which protection is sought by the wording of diseases that are caused, mediated and/or propagated by AMPK activity. In particular, the disclaimer shall be valid if the compounds of generic formula (I) in their entirety as defined in claim 1 are applied in treatment, whereas the disclaimer is void for specified compounds, preferably 5,6-dihydro-4-dimethylamino-2-imino-6-methyl-1,3,5-triazine or derivatives thereof. It is consequently a preferred embodiment of the invention that the diseases are selected from the group of metabolic syndrome, renal hypertrophy, renal failure, diabetic nephropathy, cancer, inflammation, cardiovascular disease and aging, and a highly preferred embodiment that the diseases are selected from the group of renal hypertrophy and diabetic nephropathy.

Insulin resistance has become a highly prevalent condition in the general public, with enormous consequences for the public health system. It is defined as the reduced, non-adequate response of the body to the normal actions of insulin. Insulin resistance is an important risk factor for the development of cardiovascular disease and Type II diabetes mellitus (T2DM). Diabetes is a chronic disease with many pathological manifestations. It is accompanied by disorders of lipid and sugar metabolism as well as circulatory disorders. In addition, insulin resistance is associated with a variety of cardio-vascular risk-factors (e.g. obesity, dyslipidemia, hypertension and blood clotting disturbances) that when exhibited collectively is referred to as the metabolic syndrome or syndrome X. Thus, insulin resistance syndrome (syndrome X) is characterized especially by a reduction in the action of insulin (Presse Médicale 26, 671 (1997)) and is involved in many pathological conditions as mentioned above, particularly diabetes, more particularly non-insulin dependent diabetes, but additionally certain macro-vascular complications or micro-vascular complications. Considerable evidence now exists that insulin resistance may be the unifying causal factor underlying the metabolic syndrome (Turner & Hellerstein, Curr Opin Drug Discovery & Develop 8, 115 (2005)).

In a more preferred embodiment of the invention, the diseases are renal hypertrophy and/or diabetic nephropathy. The medical indication "hypertrophy" is the increase of the size of an organ or in a select area of the tissue. It is to be distinguished from hyperplasia which occurs due to cell division increasing the number of cells while their size stays the same, whereas hypertrophy occurs due to an increase in the size of cells while the number stays the same. In the present invention, the renal hypertrophy shall be particularly regarded in conjunction with diabetes, i.e. induced thereby, such as early stages of insulin deficient diabetes, e.g. insulin dependent diabetes mellitus (IDDM).

In a most preferred embodiment of the invention, the disease is diabetic nephropathy. Said medical indication relates to diseases of the kidney and kidney function, which are mainly caused non-inflammatorily. The challenging subtype in the scope of the invention is reflected by diabetic nephropathy (nephropatia diabetica), which is also known as Kimmelstiel-Wilson syndrome and intercapillary glomerulonephritis. Diabetic nephropathy is the most common cause of end stage in a renal disease. It is a progressive kidney disease caused by angiopathy of capillaries in the kidney glomeruli, and characterized by nephrotic syndrome and nodular glomerulosclerosis. It is due to longstanding diabetes mellitus, and is a prime cause for dialysis in many Western countries. In more detail, the loss of podocytes is an early phenomenon triggering the initiation of glomerular lesions. The increase in podocyte apoptosis is preceded by increases in proteinuria, mean glomerular and mesangial areas as well as by a drop in glomerular density and synaptopodin content. The ROS production induced by hyperglycemia could also be involved in podocyte apoptosis and depletion.

The invention also relates to the use of at least one compound of formula (I) as defined according to the invention and/or physiologically acceptable salts thereof for the prophylactic or therapeutic treatment and/or monitoring of diseases that are caused, mediated and/or propagated by AMPK activity. Furthermore, the invention relates to the use of at least one compound of formula (I) as defined according to the invention and/or physiologically acceptable salts thereof for the manufacture of a medicament for the prophylactic or therapeutic treatment and/or monitoring of diseases that are caused, mediated and/or propagated by AMPK activity. The medicament can be used to prevent the initiation of diseases associated with AMPK activity in advance or to treat the arising and continuing symptoms. The diseases as concerned by the invention are preferably renal hypertrophy and/or diabetic nephropathy. In addition, the prior teaching of the present specification concerning the purpose-related compounds is valid and applicable without restrictions to the use of the compounds and its salts for the manufacture of a medicament for prophylaxis and therapy of said diseases.

Object of the present invention is also the use of at least one compound of formula (I) as defined according to the invention and/or physiologically acceptable salts thereof for activating AMPK. In the meaning of the invention, "activity" is a function or set of functions performed by AMPK in a biological context, i.e. within a cell. "Activating" refers to parameter values that exceed initial reading, within a normal statistical range as caused by the measurement method and the fact of a living organism involved. The increase in activity can be based on the up-regulation of AMPK synthesis, the modification of existing AMPK or a combination of both mechanisms. The AMPK yield can be especially increased by promoting synthesis on the level of transcription and/or translation. Furthermore, the AMPK gene or gene products thereof can be up-regulated by manipulating regulatory components of AMPK expression and/or signal transduction pathways involved in AMPK expression. It is preferred, however, to modify existing AMPK protein, more particularly to increase AMPK phosphorylation.

The AMPK activity is preferably enhanced at least 30%, more preferably at least doubled, most preferably at least tripled, and highly preferably at least quadrupled. Such increase is preferably obtained if the compound of formula (I) is provided for administration in a dose range from 5 to 500 mg, more preferably in a dose range from 15 to 200 mg/kg. The use may be either performed in-vitro or in-vivo models. The in-vitro use is preferably applied to samples of humans suffering from renal hypertrophy and/or diabetic nephropathy, more preferably diabetic nephropathy. For example, testing of several compounds of formula (I) makes the selection of that compound possible that is best suited for the treatment of the mammalian subject. The in-vivo dose rate of the chosen tetrahydrotriazine compound is advantageously pre-adjusted to the severity of diabetic nephropathy of the respective specific cells with regard to the in-vitro data. Therefore, the therapeutic efficacy is remarkably enhanced. Moreover, the prior teaching of the present specification concerning the purpose-related compounds of the invention is considered as valid and applicable without restrictions to the use of the compounds for the activation of AMPK if expedient.

It is another object of the invention to use the compound of formula (I) as defined herein and/or physiologically acceptable salts thereof for enhancing glucose homeostasis. As set forth above, the decreased expression of gluconeogenic enzymes reduces hepatic glucose output and improves overall glucose homeostasis, and both direct inhibition and/or reduced expression of key enzymes in lipid metabolism increases glucose uptake and fatty acid oxidation with resulting improvement of glucose homeostasis and, due to a reduction in intra-myocyte triglyceride accumulation, improved insulin action.

It is still another object of the invention to use the compound of formula (I) as defined herein and/or physiologically acceptable salts thereof for decreasing podocytopathy. Podocytes are cells of the visceral epithelium in the kidneys, which form a crucial component of the glomerular filtration barrier. Their contribution is size selectivity, and they maintain a massive filtration surface. The term "podocytopathy" refers to the dysfunction of said podocytes, which is translated by increased proteinuria, ROS production and/or reduced synaptopodin content, and culminates in the apoptosis in glomerular cells (podocytes). The compounds of formula (I) have been revealed to improve the podocytopathic behavior, particularly in cellular systems of single cells, cell cultures, tissues, organs or mammals, each with diabetic disorders, such that the apoptosis rate is slowed, diminished or stopped, or proliferation is even induced. The glomerular expression of synaptopodin and/or laminin represents preferred parameters for assessing podocytopathy, wherein change in a single or both parameters indicates decreased podocytopathy such that the glomerular expression of synaptopodin is increased and/or the glomerular expression of laminin is decreased. In particular, the synaptopodin expression is increased, preferably at least 10%, more preferably at least 20%, and most preferably at least 30%. In a highly preferred aspect of the present invention, the glomerular expression of synaptopodin is restored, i.e. at the same level like a healthy cellular system. The prior teaching of the present specification concerning the purpose-related compounds of the invention and their use for activating AMPK is considered as valid and applicable without restrictions to the use of the compounds for decreasing podocytopathy along with increasing synaptopodin expression if expedient.

Still another object of the invention is the use of the compound of formula (I) as defined herein and/or physiologically acceptable salts thereof for decreasing the production of reactive oxygen species (ROS). In a preferred embodiment of the present invention, the ROS production is decreased at least 10%, more preferably at least 20%, most preferably at least 30%, and highly preferably at least 40%. The prior teaching of the present specification concerning the purpose-related compounds of the invention and the use thereof is considered as valid and applicable without restrictions to the use of the compounds for decreasing ROS production if expedient.

Further, the invention may be practiced as a method for treating diseases that are caused, mediated and/or propagated by AMPK activity, wherein an effective amount of at least one compound of formula (I) as defined according to the invention and/or physiologically acceptable salts thereof is administered to a mammal in need of such treatment. The mammals to be treated are humans in particular. The preferred treatment is an oral or parenteral administration. The treatment of the patients suffering from renal hypertrophy and/or diabetic nephropathy, preferably diabetic nephropathy, or people bearing a risk of developing such diseases on the basis of inhibited AMPK by means of the tetrahydrotriazine compounds of formula (I) slows the progression of kidney damage and controls related complications in these individuals. Such improvement is preferably obtained if the compound of formula (I) is administered in a dose range from 25 to 100 mg per kg of body weight, more preferably 50 mg per kg of body weight. In another preferred aspect, the triazine compound 5,6-dihydro-4-dimethylamino-2-imino-6-methyl-1,3,5-triazine is used at different doses, more preferably 5,6-dihydro-4-dimethylamino-2-imino-6-methyl-1,3,5-triazine hydrochloride. The prior teaching of the invention and its embodiments is valid and applicable without restrictions to the method of treatment if expedient.

A further object of the present invention is the use of synaptopodin as biomarker for podocytopathy.

The invention also teaches a method for screening compounds, which reduce podocytopathy, comprising the steps of:

providing a cellular system or a sample thereof, whose podocytes are capable of expressing synaptopodin, wherein the system is selected from the group of single cells, cell cultures, tissues, organs and mammals, incubating at least a portion of the system with compounds to be screened, correlating an amount of signal or change in signal with a synaptopodin concentration in the system, detecting a level of podocytopathy by comparing the synaptopodin concentration with another synaptopodin concentration in a control cellular system of non-apoptotic and/or apoptotic podocytes, and optionally detecting the specific interaction of compounds, which reduce podocytopathy, with an ampk gene or a regulator gene thereof, or a product of any of said genes, or a component of a signal transduction pathway comprising any of said genes or a gene product thereof.

In the first step, a cellular system is provided. The cellular system is defined to be any subject provided that the subject comprises cells. Hence, the cellular system can be selected from the group of single cells, cell cultures, tissues, organs and mammals. The scope of the cellular system also comprises parts of such biological entities, i.e. samples of tissues, organs and mammals. It shall be understood that each cellular system in the aforementioned order represents a sample of the respective following system. Particularly, the cellular sample is taken in-vivo or in-situ from a mammal to be tested. The withdrawal of the cellular sample follows good medical practice. Biological samples may be taken from any kind of biological species, but the sample is especially taken from a laboratory animal or a human, more preferably a rat, mouse or human, most preferably a human. In the present invention, the cellular system may also comprise a biological fluid, wherein the sample of body fluid preferably consists of blood, serum, plasma, saliva or urine. It is also preferred to gather a tissue sample by biopsy, especially taken close to the location of ailment. The biological samples can be originated from any tissue, such as the uterus, pituitary gland, liver, brain, colon, breast, adipose tissue, etc. The sample may be purified to remove disturbing substances, such as inhibitors for the formation of hydrogen bonds.

The cell sample refers to any type of primary podocytes or genetically engineered podocytes, either in the isolated status, in culture or as cell line, provided that they are capable of expressing synaptopodin. Synaptopodin represents a new class of actin-binding proteins, which has been localized in podocytes and a subset of telenecephalic postsynaptic densities first. It is another aspect of the present invention to use synaptopodin as biomarker for podocytopathy. Decrease in synaptopodin clearly indicates loss of podocytes function. Such finding forms the basis for the screening method according to the invention.

As obvious to the skilled artisan, the present invention shall not be construed to be limited to the full-length protein synaptopodin. Physiological or artificial fragments of synaptopodin, secondary modifications of synaptopodin, species-dependent alterations as well as allelic variants of synaptopodin are also encompassed by the present invention. In this regard an "allelic variant" is understood to represent the gene product of one of two or more different forms of a gene or DNA sequence that can exist at a genetic single locus. Artificial fragments preferably encompass a peptide produced synthetically or by recombinant techniques. Such a fragment may be advantageously used as a standard in an immunoassay. Preferably, full-length synaptopodin or a physiological variant of this marker is detected in a method according to the present invention. It shall also be understood, consequently, that variants, mutants, parts or homologous protein sequences of synaptopodin having the same function, are included in the scope of definition as well as protection. The degree of alteration between the original sequence and its derivatives is inevitably limited by the requirement of substrate recognition and methionine cleavage. Preferably, the homology amounts to at least 85%, more preferably at least 95%, most preferably at least 98%. Possible alterations comprise deletion, insertion, substitution, modification and addition of at least one amino acid, or the fusion with another protein acid. The engineered cells are capable of expressing the synaptopodin protein by transfection with appropriate vectors harboring the corresponding gene or parts thereof. Preferably, the recombinant cells are of eukaryotic origin.

The cell sample is stored, such as frozen, cultivated for a certain period or immediately subjected to second step. Before incubating it with compounds to be screened, the cell sample is divided into multiple portions. At least two portions are provided; one is used for screening while the other one serves as control. Preferably, the number of portions for screening exceeds the number of control portions. Usually, numerous portions are subjected to a high-throughput screening.

As used herein, "compounds which reduce podocytopathy" are agents that block at least apoptosis of podocytes, which refers to any factor, agent, compound whether endogenous or exogenous in origin, which is capable of binding and interacting with AMPK and thereby stopping certain biological effects of AMPK. The compounds are composed of biological and/or chemical structures capable to interact with a target molecule. Herein, any component of AMPK signaling shall be considered as "target molecule", which is not limited to the AMPK protein target, but may also comprise the coding gene or any gene product thereof, a regulator protein, or a component of a signal transduction pathway comprising said gene or gene products thereof. Consequently, the specific interaction of compounds may involve either the mere targeting or the induction of alterations in cell function, or it may even include both effects simultaneously.

The compounds to be screened in the inventive method are not restricted anyway. In particular, the compounds are selected from the group of nucleic acids, peptides, carbohydrates, polymers, small molecules having a molecular weight between 50 and 1.000 Da and proteins. These compounds are often available in libraries. It is preferred to incubate a single compound within a distinct portion of the cell sample. However, it is also possible to investigate the cooperative effect of compounds by incubating at least two compounds within one portion. A further portion of cells is simultaneously incubated in the absence of the compounds. The term "incubation" denotes the contacting of the compounds with the cells for a distinct period, which depends on the kind of compounds and/or target. The incubation process also depends on various other parameters, e.g. the cell type and the sensitivity of detection, which optimization follows routine procedures known to those skilled in the art. The incubation procedure can be realized without a chemical conversion or may involve a biochemical reaction. Adding chemical solutions and/or applying physical procedures, e.g. impact of heat, can improve the accessibility of the target structures in the sample. Specific incubation products are formed as result of the incubation.

In the next steps, the identification of effective compounds in the meaning of the invention is indirectly performed by determining the presence of synaptopodin. The determination is performed at a specified moment and correlated to the signal strength at the beginning of the experiment and the positive/negative control. Either the control system is not incubated with the compounds (negative control) or the control system is incubated with a standard compound having no AMPK activating activity (negative control) or a standard compound having AMPK activating activity (positive control). The activity is revealed by a change in protein concentration. Pair-wise comparisons are made between each of the treatments. A pair-wise comparison involves the protein concentration data for the given biomarker synaptopodin under a given treatment condition compared to the protein concentration data for this protein under a second treatment condition. The comparison is performed using suitable statistical technique with the assistance of known and commercially available programs.

The detection may be performed by applying the intact cell to a detection method of choice. It is preferred, however, to provide cellular extracts first. Cell lysis can be performed in suitable, well-known lysis buffers, which may cause an osmotic shock and perforate the cell membrane. The stability of the cell structure can also be destroyed by mechanical forces, such as ball mill, French press, ultrasonic, etc., by enzymatic degradation of cell wall and cell membrane, respectively, and/or by the action of tensides. The biomarker may be further purified to remove disturbing substances or the biomarker synaptopodin can be concentrated in the sample. Downstream-processing and/or concentrating are preferably performed by the method of precipitation, dialysis, gel filtration, gel elution, or chromatography, such as HPLC or ion exchange chromatography. It is recommended to combine several methods for better yields.

Suitable tests for detecting synaptopodin inhibition are known to those skilled in the art or can be easily designed as a matter of routine. Many different types of assays are known, examples of which are set forth below. Although the assay according to the invention may be any assay suitable to detect and/or quantify gene expression, synaptopodin is preferably determined by means of substances specifically interacting with synaptopodin. The term "specific substances" as used herein comprises molecules with high affinity to at synaptopodin in order to ensure a reliable binding. The substances are preferably specific to parts of the protein. Such parts represent a restriction to those regions which are sufficient for the expression of a specific function, i.e. the provision of a structural determinant for recognition. All truncations are inevitably limited by the requirement of preserving the unique recognition. However, the parts of the gene products can be very small. Preferably, the substances are mono-specific in order to guarantee an exclusive and directed interaction with the chosen single target.

The recognition of the protein or N-terminal parts thereof according to the invention can be realized by a specific interaction with substances on the primary, secondary and/or tertiary structure level of an amino acid sequence. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, interactions between epitope and antibody binding site, nucleotide base pairing, and the like. Such association may also encompass the presence of other molecules such as peptides, proteins or other nucleotide sequences.

The specific substances are composed of biological and/or chemical structures capable to interact with the target molecule in such a manner that makes a recognition, binding and interaction possible. In particular, the substances are selected from the group of nucleic acids, peptides, carbohydrates, polymers, small molecules having a molecular weight between 50 and 1.000 Da and proteins, preferably nucleic acids and proteins. The proteins or peptides are more preferably selected from the group consisting of antibodies, cytokines, lipocalins, receptors, lectins, avidins, lipoproteins, glycoproteins, oligopeptides, peptide ligands and peptide hormones. Most preferably, antibodies are used as specific substance. Highly preferably, the antibody clone G1D4 recognizes differentiated podocytes (glomerular visceral epithelial cells). The nucleic acids are more preferably single or double stranded DNA or RNA, primers, antisense oligonucleotides, ribozymes, DNA enzymes, aptamers and/or siRNA, or parts thereof. The nucleic acids can be optionally modified as phosphorothioate DNA, locked nucleic acid (LNA), peptide nucleic acid (PNA) or spiegelmer. The specific substances express a sufficient sensitivity and specificity in order to ensure a reliable detection. A specific substance has at least an affinity of $10^{-7}$ M for its corresponding target molecule. The specific substance preferably has an affinity of $10^{-8}$ M or even more preferred of $10^{-9}$ M for its target molecule. As the skilled artisan will appreciate the term specific is used to indicate that other biomolecules present in the sample do not significantly bind to the substance specific for synaptopodin. Preferably, the level of binding to a biomolecule other than the target molecule results in a binding affinity of only 10% of the affinity of the target molecule, more preferably only 5% or less. A most preferred specific substance will fulfill both the above minimum criteria for affinity as well as for specificity.

The specific substances can be labeled, in doing so the labeling depends on their inherent features and the detection method to be applied, i.e. the required sensitivity, ease of conjugation, stability requirements, and available instrumentation and disposal provisions. A labeling method is not particularly limited as long as a label is easily detected. A "labeled specific substance" is one that is bound, either covalently through a linker or a chemical bond, or non-covalently through ionic, van der Waals, electrostatic, hydrophobic interactions or hydrogen bonds, to a label such that the presence of the synaptopodin may be detected by detecting the presence of the label bound to the biomarker. The applied methods are well-known to the skilled artisan. Preferred examples of suitable detection methods according to the present invention are luminescence, particularly fluorescence, furthermore VIS coloring and/or radioactive emission.

Provided that the cellular system of the invention is incubated with various concentrations of a potential AMPK activator, the amount of emitted signal or change in signal observed in the presence of the activator is indicative of the change in activity experienced by the compound. The change in signal is a change in the signal intensity and/or the signal lifetime. It does not matter whether the change in signal results in a decrease or increase of the signal. Even the loss of any signal is regarded as change in signal. The signal amount or change, respectively, can be then related to the concentration of the activator in the sample, i.e. the calibration curve enables the meter-reading of a matching concentration. Preferably, the calibration curve is based on the Lambert-Beer equation if using UV/VIS coloring or luminescence. The concentration of the biomarker is subsequently calculated by considering the molar part of synaptopodin within the product complex if present. Preferably, the molar ratio of specific substance and synaptopodin is 1:1, which is present in antibody/synaptopodin complexes for instance, so that the molar concentration of the incubation products corresponds to the molar concentration of synaptopodin.

Efficacy of compounds is diagnosed by comparing the concentration of synaptopodin in the sample with known synaptopodin concentration levels of either non-apoptotic cells and/or apoptotic cells. It shall be understood that the known concentrations are statistically proven, therefore representing a certain level or range, respectively. Any measured concentration, which differs from the synaptopodin concentration level of non-apoptotic cells and/or is equal to the synaptopodin concentration level of apoptotic cells, indicates an abnormality of the tested cell sample. It is desired to measure concentrations, which are higher than the gene product concentration level of apoptotic cells, for detecting podocytopathy inhibition. Using this method, the inventors demonstrated sensitivity to sub-micromolar or even nanomolar concentrations. The calibration plot reveals that the method can be applied in a dynamic range that spans over a couple of magnitude.

Among those compounds being revealed to reduce podocytopathy, each or some representatives are selected for further analysis. In a preferred embodiment of the present invention, the screening method involves another step, which comprises the detection of the specific interaction of compounds with an ampk gene or a gene product thereof, or an associated regulator gene or a gene product thereof for regulating said ampk gene, particularly a regulator protein, or a component of a signal transduction pathway comprising any of said genes or a gene product thereof, provided that the aforementioned interaction results in the decrease or even depletion of apoptosis. It is preferred to detect the specific binding of compounds to the AMPK protein target. Preferably, the compounds showing the greatest discrepancy to the control are chosen. They are analyzed for specificity to exclude another signal transduction, which is not initiated by the binding to the AMPK protein target of the invention or associated molecules thereof, and additionally tested for such cross-reactivity in order to prevent adverse reactions or other effects by linked pathways if simultaneous docking to further target structures occurs. Several methods are known in the field of the art for detecting specific and/or mono-specific binding, such as gel shift experiments, Biacore measurements, X-ray structure analysis, competitive binding studies, and the like. In a preferred embodiment of the screening method, the mono-specific binding of substances to the target structures of the invention is detected.

The invention also relates to a method for in-vitro diagnosing diabetic nephropathy comprising the steps of:
incubating a sample of podocytes taken from a mammal with substances being specific to synaptopodin,
determining specific incubation products,
correlating an amount of signal or change in signal with a synaptopodin concentration in the sample, and
detecting diabetic nephropathy by comparing the synaptopodin concentration with another synaptopodin concentration in a sample of non-apoptotic and/or apoptotic podocytes, wherein the stage of diabetic nephropathy and the synaptopodin concentration are inversely proportional.

Presently, the diagnosis is suspected when a routine urinalysis of a person with diabetes shows too much protein in the urine. The earliest indication of microalbuminuria is not detectable by conventional urine test strips, but it requires the laborious urine collection for 24 hours and subsequent albumin determination. By means of the inventive method, the trigger of loosing podocycles is correlated to the initiation of diabetic nephropathy, which makes an early diagnosis possible. The inverse proportionality can follow either a linear or a non-linear function. Moreover, the prior teaching concerning the method for screening compounds is valid and applicable without restrictions to the method for in-vitro diagnosing diabetic nephropathy if expedient.

In the scope of the present invention, potential drugs comprising tetrahydrotriazine compounds of formula (I) are provided for the prophylactic or therapeutic treatment and/or monitoring of diseases that are caused, mediated and/or propagated by AMPK activity for the first time. The invention addresses the successful evaluation of in-vivo effects of tetrahydrotriazine compounds in general and 5,6-dihydro-4-dimethylamino-2-imino-6-methyl-1,3,5-triazine in particular on present diseases induced by diabetes as well as on functionality induced by hyperglycemia. More particularly, the diseases are renal hypertrophy in early stages of diabetes and/or diabetic nephropathy due to longstanding diabetes mellitus, the latter representing the end stage of a renal disease thereby. As result of administering the compounds according to the invention, AMPK is significantly activated. Tetrahydrotriazine compounds of formula (I) are indirect activators of AMPK. The mTOR activation in diabetic models of type 1 (STZ rats) and type 2 (db/db mice) induces renal hypertrophy while AMPK activation reverses mTOR activation and inhibits renal hypertrophy. Hence, this effect can be used for the treatment of renal hypertrophy induced by diabetes in patients. Furthermore, apoptosis in glomerular cells (e.g. demonstrated in STZ rats) is preceded by increases in proteinuria and reduction of content in synaptopodin translating dysfunction of podocytes. Since the decrease in synaptopodin has been revealed to indicate the loss of podocytes function, which triggers glomerular lesions, said biomarker is superior to conventional methods for testing microalbuminuria and in-vitro diagnosing diabetic nephropathy early. The glomerular content of synaptopodin is at least partially or even completely restored by the impact of present tetrahydrotriazine derivatives, such as exemplarily shown in diabetic ZDF rats, and podocytopathy is improved. Hence, said compounds of formula (I) can be advantageously used for the treatment of diabetic nephropathy in both types of diabetic patients. A treatment with such tetrahydrotriazine derivatives is of special benefit for the decrease of ROS production. The use of the compounds is a promising, novel approach for a broad spectrum of therapies causing a direct and immediate reduction of symptoms. The impact is of special benefit to efficiently combat illnesses arising from AMPK activity. The compound and derivatives thereof are characterized by a high specificity and stability; low manufacturing costs and convenient handling. These features form the basis for a reproducible action, wherein the lack of cross-reactivity and adverse effects is included, and for a reliable and safe interaction with their matching target structures.

All the references cited herein are incorporated by reference in the disclosure of the invention hereby.

It is to be understood that this invention is not limited to the particular methods, specific substances, uses and kits described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a salt" includes a single or several different salts and vice versa, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again if the technical problem of the invention is solved.

In the following Figures and Tables, the compound 5,6-dihydro-4-dimethylamino-2-imino-6-methyl-1,3,5-triazine is abbreviated as EMD008.

EXAMPLE 1

Preparation of 4-amino-3,6-dihydro-2-dimethylamino-6-methyl-1,3,5-triazine hydrochloride Above and below, all temperatures are given in ° C. In the following examples, "conventional work-up" means: if necessary, water is added, the pH is, if necessary, adjusted to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallization.

A) Comparative experiment: A mixture of 250.2 g of metformin hydrochloride, 213.6 g of acetaldehyde diethyl acetal and 12.5 g of toluene-4-sulfonic acid monohydrate in 500 ml of isobutanol was heated under reflux for 40 hours. Some of the solvent was removed by distillation. The mixture was cooled to 10° C., and the white precipitate was separated off, giving 224.7 g (77.4%) of 4-amino-3,6-dihydro-2-dimethylamino-6-methyl-1,3,5-triazine hydrochloride.

B) Synthesis according to the invention: A mixture of 1002.6 g of metformin hydrochloride, 359.1 g of paraldehyde and 51.6 g of toluene-4-sulfonic acid monohydrate in 2405.9 g of isobutanol was heated under reflux for 6 hours. Some of the solvent was removed by distillation. The mixture was cooled to 12° C., and the white precipitate was separated off, giving 953.8 g (81.4%) of 4-amino-3,6-dihydro-2-dimethylamino-6-methyl-1,3,5-triazine hydrochloride.

C) Synthesis according to the invention: A mixture of 100.1 g of metformin hydrochloride, 36.5 g of paraldehyde and 4 g of Dowex DR-2030 in 237.8 ml of isobutanol was heated under reflux for 6 hours. The catalyst was subsequently filtered off, and some of the solvent was removed by distillation. The remainder of the solution was cooled to 10-15° C., and the white precipitate was separated off, giving 93.5 g (80.7%) of 4-amino-3,6-dihydro-2-dimethylamino-6-methyl-1,3,5-triazine hydrochloride.

EXAMPLE 2

Figure 1:
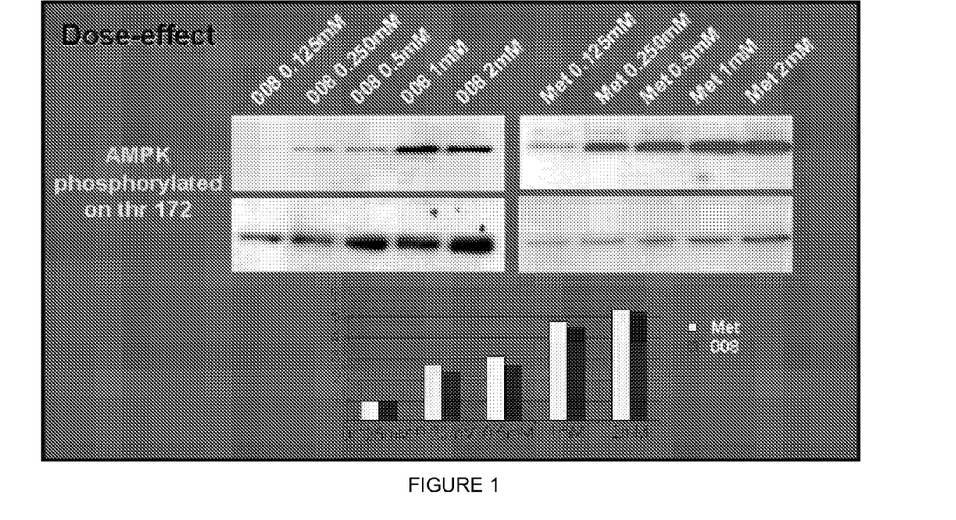
FIG. 1 shows the qualitative AMPK activation after treatment of hepatocyte cells with different doses of metformin and 5,6-dihydro-4-dimethylamino-2-imino-6-methyl-1,3,5-triazine, respectively. The AMPK activation in hepatocytes is given in the gel electrophoresis pictures. The supplemental diagram visualizes the degree of AMPK activation in hepatocytes quantitatively.
Figure 2:
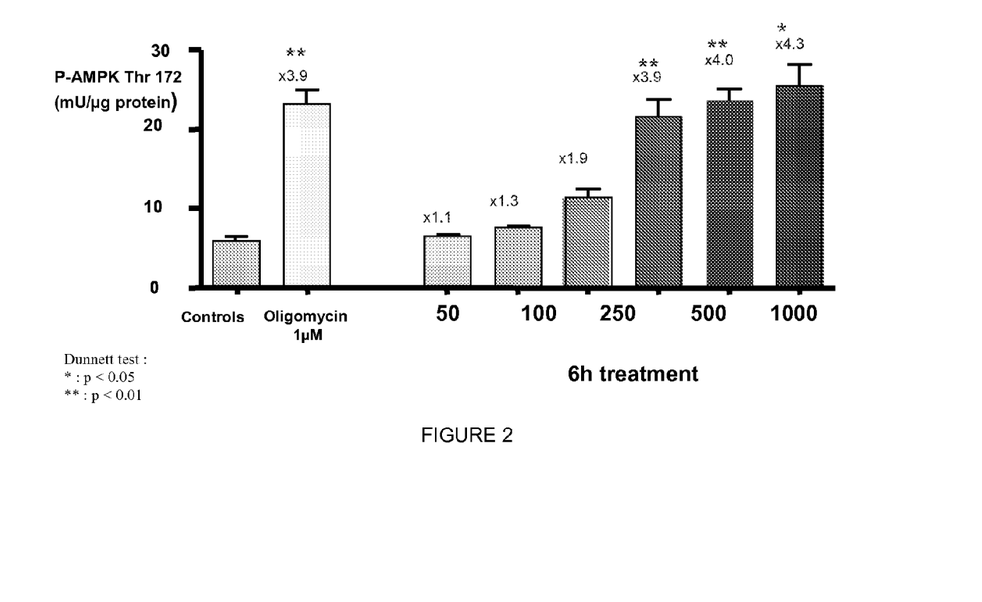
FIG. 2 shows the quantitative AMPK activation after treatment of muscle cells with different doses of 5,6-dihydro-4-dimethylamino-2-imino-6-methyl-1,3,5-triazine.

AMPK Activation 5,6-dihydro-4-dimethylamino-2-imino-6-methyl-1,3,5-triazine showed a significant activation of AMPK. This activation was observed in hepatocyte cells (FIG. 1) and in muscle cells. Metformin and 5,6-dihydro-4-dimethylamino-2-imino-6-methyl-1,3,5-triazine exhibited a similar AMPK activation of AMPK in hepatocytes. In muscle cells, 5,6-dihydro-4-dimethylamino-2-imino-6-methyl-1,3,5-triazine significantly increased AMPK activity (FIG. 2). This effect was also dose dependent and even stronger than metformin's effect.

EXAMPLE 3

Synaptopodin Expression Content

Synaptopodin (G1D4) was detected with a monoclonal mouse IgG antibody (#61094, Progen). For each rat, 40 glomeruli out of two consecutive sections were selected at random. The synaptopodin (G1D4) positive area in the mesangium was measured with the Ariol SL-50 automated microscope (Applied Imaging Int. Ltd.) scanning sections at X20 (scale x/y: 1 pixel=0.36×0.36 $\mu m^2$) and setting a circular measure field of 2400 $\mu m^2$ in the centre of the glomerulus. The positive labeled area of synaptopodin (G1D4) was calculated as percentage of tissue area in the measure field. For each animal, the mean out of 40 glomeruli was calculated. Statistical comparisons were performed by unpaired Mann-Whitney-test. Data are mean±SEM.

Figure 3:
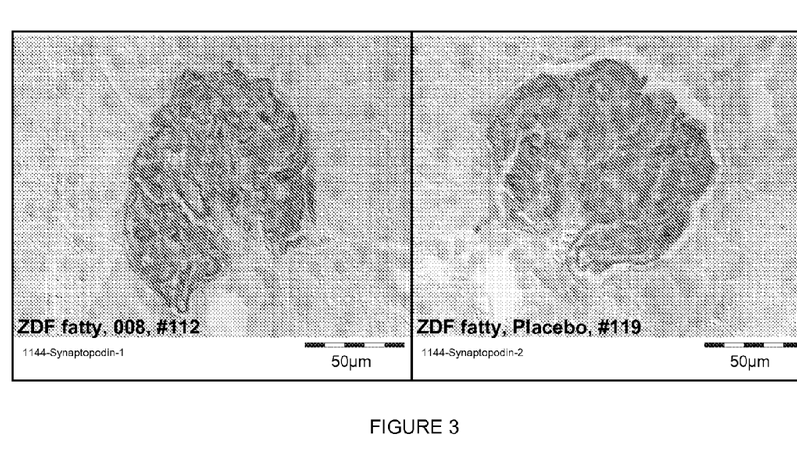
FIG. 3 shows synaptopodin labeling in the glomeruli of ZDF fatty rats after treatment with 5,6-dihydro-4-dimethylamino-2-imino-6-methyl-1,3,5-triazine and a placebo, respectively.

The antibody clone G1D4 recognized differentiated podocytes (glomerular visceral epithelial cells). The antibody labeled synaptopodin in rat glomeruli with good contrast (FIG. 3). In ZDF fatty rats at the age of 19 weeks, the glomerular fraction of synaptopodin was decreased in comparison with ZDF lean rats (Table 1). Treatment with metformin had no effect on the glomerular fraction of synaptopodin. After treatment with 5,6-dihydro-4-dimethylamino-2-imino-6-methyl-1,3,5-triazine, the glomerular fraction of synaptopodin was moderately increased.

TABLE 1

Glomerular synaptopodin (G1D4) fraction (% positive area) in the kidney of rats

| Group | Drug | Dose | Positive Area (%) | N | P |
|---|---|---|---|---|---|
| 1 - ZDF lean | Placebo | Placebo | 45 ± 4 | 11 | |
| 2 - ZDF fatty | Placebo | Placebo | 34 ± 3 | 11 | <0.05 vs group 1 |
| 5 - ZDF fatty | Metformin | 2 × 25 mg/kg/d p.o. | 38 ± 4 | 12 | NS vs group 2 |
| 8 - ZDF fatty | EMD 387008 | 2 × 25 mg/kg/d p.o. | 45 ± 3 | 11 | <0.05 vs group 2 |

EXAMPLE 4

Production of Reactive Oxygen Species (ROS)

Figure 4:
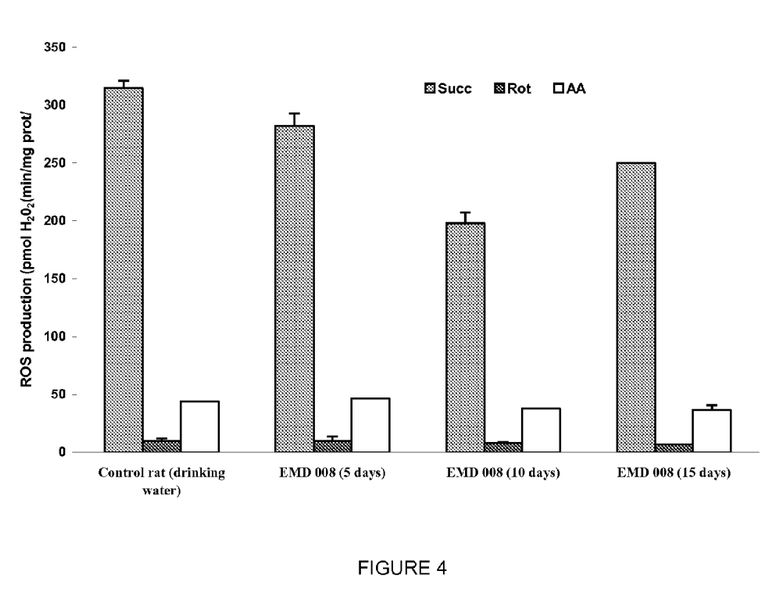
FIG. 4 shows the ROS production in the rat liver after oral administration of 5,6-dihydro-4-dimethylamino-2-imino-6-methyl-1,3,5-triazine.

The efficacy of 5,6-dihydro-4-dimethylamino-2-imino-6-methyl-1,3,5-triazine was tested if once administrated (50 mg/kg/day) to drinking water of fasted Wistar rats for at least 10 days. This approach was more physiological than subcutaneous injection at elevated dose. 5,6-dihydro-4-dimethylamino-2-imino-6-methyl-1,3,5-triazine time-dependently inhibited the ROS production linked to the reverse electron flux through complex I, i.e. in the presence of succinate alone or in combination with glutamate/malate. The effect was observed both in rat liver (FIG. 4) and in human microvascular endothelial cells (HMEC; Table 2).

TABLE 2

ROS production in HMEC-1 after administration of 5,6-dihydro-4-dimethylamino-2-imino-6-methyl-1,3,5-triazine.
$H_2O_2$ (pmol/min/$10^7$ HMEC-1 cells)

| Additions | Glutamate + Malate (GM) | | Succinate (S) | | GMS | |
|---|---|---|---|---|---|---|
| | Control | EMD008 | Control | EMD008 | Control | EMD008 |
| None | 32.3 ± 2.4 | 28.4 ± 2.2 | 25.7 ± 3.0 | 14.5 ± 1.3* | 22.3 ± 1.5 | 15.7 ± 1.4* |
| Rotenone (Rot) | 38.3 ± 3.2 | 37.5 ± 1.5 | 10.7 ± 1.8 | 11.4 ± 2.7 | 7.8 ± 0.9 | 6.9 ± 1.1 |
| Rot + antimycin A (AA) | 51 ± 4.8 | 51.4 ± 8.7 | 20.1 ± 3.3 | 19.1 ± 3.2 | 20.5 ± 1.4 | 18.6 ± 1.3 |

EXAMPLE 5

Pharmaceutical Preparations

A) Injection vials: A solution of 100 g of active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

B) Suppositories: A mixture of 20 g of active ingredient according to the invention was melted with 100 g of soya lecithin and 1400 g of cocoa butter, poured into moulds and allowed to cool. Each suppository contained 20 mg of active ingredient.

C) Solution: A solution was prepared from 1 g of active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

D) Ointment: 500 mg of active ingredient according to the invention were mixed with 99.5 g of Vaseline under aseptic conditions.

E) Tablets: A mixture of 1 kg of active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient. Other tablets with the active ingredient 5,6-dihydro-4-dimethylamino-2-imino-6-methyl-1,3,5-triazine were prepared according to the Tables 3-8.

TABLE 3

Tablet containing 87% triazine derivative and adjuvants

|  | mg | % |
| --- | --- | --- |
| 5,6-dihydro-4-dimethylamino-2-imino-6-methyl-1,3,5-triazine | 200 | 87.0 |
| Lactose | 10.5 | 4.6 |
| Starch | 5.7 | 2.5 |
| Crospovidone | 5.7 | 2.5 |
| Talc | 7 | 3.0 |
| Magnesium stearate | 1.1 | 0.5 |
| Total | 230 | 100.0 |

TABLE 4

Tablet containing 43.5% triazine derivative and adjuvants

|  | Mg | % |
| --- | --- | --- |
| 5,6-dihydro-4-dimethylamino-2-imino-6-methyl-1,3,5-triazine | 100 | 43.5 |
| Mannitol | 50.5 | 22.0 |
| Avicel ph 102 | 60 | 26.1 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 5

Tablet containing 21.7% triazine derivative and adjuvants

|  | Mg | % |
| --- | --- | --- |
| 5,6-dihydro-4-dimethylamino-2-imino-6-methyl-1,3,5-triazine | 50 | 21.7 |
| Mannitol | 80.5 | 35.0 |
| Avicel ph102 | 80 | 34.8 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 6

Tablet containing 87% triazine derivative and adjuvants

|  | mg | % |
| --- | --- | --- |
| 5,6-dihydro-4-dimethylamino-2-imino-6-methyl-1,3,5-triazine | 200 | 87.0 |
| Mannitol | 10.5 | 4.6 |
| Hydroxypropylcellulose | 5.7 | 2.5 |
| Starch | 5.7 | 2.5 |
| Talc | 7 | 3.0 |
| Magnesium stearate | 1.1 | 0.5 |
| Total | 230 | 100.0 |

TABLE 7

Tablet containing 79.4% triazine derivative and adjuvants

|  | mg | % |
| --- | --- | --- |
| 5,6-dihydro-4-dimethylamino-2-imino-6-methyl-1,3,5-triazine | 100 | 79.4 |
| Lactose | 12.2 | 9.7 |
| Hydroxypropylcellulose | 5.7 | 4.5 |
| Talc | 7 | 5.6 |
| Magnesium stearate | 1.1 | 0.9 |
| Total | 126 | 100.0 |

TABLE 8

Tablet containing 12.7% triazine derivative and adjuvants

|  | Mg | % |
| --- | --- | --- |
| 5,6-dihydro-4-dimethylamino-2-imino-6-methyl-1,3,5-triazine | 50 | 12.7 |
| Lactose | 172.2 | 43.7 |
| Avicel ph102 | 152 | 38.6 |
| Hydroxypropylcellulose | 7.1 | 1.8 |
| Sodium starch glycolate | 11.5 | 2.9 |
| Magnesium stearate | 1.2 | 0.3 |
| Total | 394 | 100 |

F) Coated tablets: Tablets were pressed analogously to the previous paragraph E) and subsequently coated in a conventional manner with a coating of sucrose, potato starch, talc, tragacanth and dye.

G) Capsules: 2 kg of active ingredient according to the invention were introduced into hard gelatin capsules in a conventional manner in such a way that each capsule contained 20 mg of the active ingredient.

H) Ampoules: A solution of 1 kg of active ingredient according to the invention in 60 l of bidistilled water was sterile filtered, transferred into ampoules, lyophilized under sterile conditions and sealed under sterile conditions. Each ampoule contained 10 mg of active ingredient.

I) Inhalation spray: 14 g of active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. A method for treating a mammal for prostate cancer, said method comprising administering a therapeutically effective amount of a compound of formula (I) and/or a physiologically acceptable salt thereof to a mammal in need of such treating wherein the compound of formula (I) is 5,6-dihydro-4-dimethylamino-2-imino-6-methyl-1,3,5-triazine and/or the physiologically acceptable hydrochloride salt thereof.

2. The method according to claim 1, wherein the compound of formula (I) is combined with at least another active ingredient.

3. The method according to claim 2, wherein the at least another active ingredient is selected from the group consisting of an ACE inhibitor, AT1 antagonist, a diuretic, HMG-CoA reductase inhibitor and a salicylate drug.

4. The method according to claim 1, wherein the compound of formula (I) is (+) 5,6-dihydro-4-dimethylamino-2-imino-6-methyl-1,3,5-triazine hydrochloride.

\* \* \* \* \*